United States Patent
Baxter, III

(10) Patent No.: US 7,457,658 B2
(45) Date of Patent: Nov. 25, 2008

(54) ALGORITHM FOR ACCURATE THREE-DIMENSIONAL RECONSTRUCTION OF NON-LINEAR IMPLANTED MEDICAL DEVICES IN VIVO

(75) Inventor: Walton W. Baxter, III, San Clemente, CA (US)

(73) Assignee: Medtronic, Inc., Minneapolis, MN (US)

( * ) Notice: Subject to any disclaimer, the term of this patent is extended or adjusted under 35 U.S.C. 154(b) by 1378 days.

(21) Appl. No.: 10/382,382

(22) Filed: Mar. 6, 2003

(65) Prior Publication Data
US 2003/0212321 A1 Nov. 13, 2003

Related U.S. Application Data

(60) Provisional application No. 60/362,534, filed on Mar. 7, 2002.

(51) Int. Cl.
A61B 5/05 (2006.01)
(52) U.S. Cl. .................. 600/426; 600/424; 600/407
(58) Field of Classification Search ......... 600/407–423, 600/424, 426, 427
See application file for complete search history.

(56) References Cited

U.S. PATENT DOCUMENTS

| | | | |
|---|---|---|---|
| 5,239,591 A | 8/1993 | Ranganath | |
| 5,471,535 A | 11/1995 | Ikezawa et al. | |
| 5,582,173 A | 12/1996 | Li | |
| 5,830,145 A * | 11/1998 | Tenhoff | 600/463 |
| 5,876,342 A | 3/1999 | Chen et al. | |
| 5,983,126 A | 11/1999 | Wittkampf | |
| 6,047,080 A | 4/2000 | Chen et al. | |
| 6,119,033 A | 9/2000 | Spigelman et al. | |
| 6,236,875 B1 | 5/2001 | Bucholz et al. | |
| 6,249,594 B1 | 6/2001 | Hibbard | |
| 2005/0197568 A1 * | 9/2005 | Vass et al. | 600/426 |
| 2005/0215887 A1 * | 9/2005 | Ben-Haim et al. | 600/424 |

FOREIGN PATENT DOCUMENTS

| | | |
|---|---|---|
| JP | 05054143 | 5/1993 |
| WO | WO 96/39660 | 12/1996 |

(Continued)

OTHER PUBLICATIONS

Baxter, WW et al., "In Vivo Finite Element Model-Based Image Analysis of Pacemaker Lead Mechanics," *Medical Image Analysis*, vol. 5, p. 255-270 (2001).

(Continued)

*Primary Examiner*—Brian L. Casler
*Assistant Examiner*—John F Ramirez
(74) *Attorney, Agent, or Firm*—Michael C Soldner

(57) ABSTRACT

A computer-implemented software system and method for performing dynamic, three-dimensional reconstruction of a non-linear implanted medical device from biplane x-ray images. A biplane radiographic image of a calibration object is used to compute the relationship between a three-dimensional coordinate system and the two-dimensional coordinate system for each image plane. These relationships are used to superimpose a three-dimensional device model onto each biplane image pair. An iterative, active contour model, initiated by a user-specified curved template, solves for the three-dimensional device centerline coordinates. Device reconstruction is repeated at each time point associated with each image pair. Algorithm output is available for test development, structural analysis or other clinically relevant applications.

12 Claims, 4 Drawing Sheets

FOREIGN PATENT DOCUMENTS

WO      WO 01/1864      11/2001

OTHER PUBLICATIONS

Glasson, F.R. et al., "Three-dimensional Regional Dynamics of the Normal Mitral Annulus During Left Ventricular Ejection," *J. Thorac. Cardiovasc. Surg.*, vol. 111, p. 574-85 (1996).

Kass, M. et al., "Snakes: Active Contour Models," *Int. J. Comp. Vis.*, vol. 1, p. 321-331 (1988).

MacKay, S.A. et al., "Graphics Methods for Tracking Three-Dimensional Heart Wall Motion," *Comput. Biomed. Res.*, vol. 15, p. 455-473 (1982).

Baxter, W. et al., "Reconstruction of Annuloplasty Devices in an Ovine Model by Biplane Videoradiography—3D Motion and Finite Element Analysis," 6th Annual Hilton Head Workshop on Prosthetic Heart Valves, Mar. 8, 2002. Hilton Head, SC, USA.

\* cited by examiner

ALGORITHM FOR ACCURATE THREE-DIMENSIONAL RECONSTRUCTION OF NON-LINEAR IMPLANTED MEDICAL DEVICES IN VIVO

RELATED APPLICATION

This application claims priority and other benefits from U.S. Provisional Patent Application Ser. No. 60/362,534, filed Mar. 7, 2002, entitled "ALGORITHM FOR ACCURATE THREE-DIMENSIONAL RECONSTRUCTION OF IMPLANTED MEDICAL DEVICES IN VIVO", incorporated herein by reference in its entirety.

FIELD OF THE INVENTION

The present invention relates to noninvasive implanted medical device motion and deformation measurement. More specifically, the invention relates to an algorithm that enables three-dimensional reconstruction of the centerline shape and motion of an implanted non-linear medical device from biplane radiographic images of the implanted device and a calibration object.

BACKGROUND OF THE INVENTION

Implantable medical devices, such as leads, vascular devices, heart valves, annuloplasty rings or bands, or other prosthetic devices, typically undergo in vitro testing and structural modeling to ensure that the device conforms to long-term performance standards. Although mechanical failure of such devices is rare, fracture or other forms of mechanical failure do occur within the implanted environment following repeated deformation due to cardiac or other bodily motion. In vitro tests and structural models are sometimes designed to mimic or exceed the deformations that a device will endure once implanted, these testing methods and structural models have not been motivated by in vivo measurements of actual device deformations.

Numerous systems and algorithms have been proposed or are available for accurate detection of anatomic surfaces in medical images and for visualizing the location of a medical device for surgical navigation. Reference is made, for example, to U.S. Pat. No. 6,119,033 issued to Speigelman et al., U.S. Pat. No. 6,236,875 issued to Bucholz et al, and U.S. Pat. No. 5,983,126 issued to Wittkampf. Algorithms are also available for performing finite element analysis for estimating stress and resultant force distributions along a geometric structure. However, an accurate method for reconstruction of an implanted non-linear medical device, such as a catheter, a stent, or a heart valve device, for example, to measure the repetitive motion and deformation of the implanted device is not available.

A method for dynamic three-dimensional reconstruction of an implanted medical device shape and motion would be valuable in designing and validating physically realistic in vitro mechanical tests and structural models. The inventor of the present invention previously developed an algorithm for non-invasive reconstruction of an initially straight cardiac lead. See Baxter W W, et al., Medical Image Analysis 2001; 5:255-270. However, highly-curved medical devices, such as annuloplasty rings or bands, stents, or catheters, for example cannot be accurately reconstructed assuming a straight or slightly curved configuration. There remains a need therefore, for an algorithm that enables reconstruction of medical devices such as stents, catheters, or heart valve devices having non-linear and highly curved geometries.

DETAILED DESCRIPTION OF THE INVENTION

The present invention provides a method for determining the centerline shape and motion of an implanted medical device as it moves through time due to cardiac, respiratory, or other physiological motion. The method includes obtaining biplane radiographic images of an implanted non-linear medical device and a calibration object placed in the imaging volume. Calibration of biplane images is performed by computing perspective transformation matrices using images of the calibration object. The transformation matrices relate the three-dimensional coordinates of the volume occupied by the calibration object to each imaging plane's local two-dimensional image coordinates.

The implanted device is reconstructed from the biplane radiographic device images and a user-initialized template of the undeformed device. Points on a user-initialized template of the non-linear device are projected onto each x-ray image pair using the transformation perspective matrices. Through an iterative process using active contours, the device model translates and deforms until it matches the biplane image pair, and the resulting device centerline coordinates are stored.

This process of determining non-linear medical device centerline position is repeated for each time point in an imaging sequence. The reconstructed centerline shape at instants throughout a selected imaging sequence can then be displayed to visualize device motion. Reconstructed centerline points are output to a text file at each time point for further analysis or evaluation which may include in vitro test development, structural model development or clinical assessment of in vivo device motion.

The algorithm provided by the present invention can be used to reconstruct a highly curved medical device such as a non-linear medical device that has been imaged using a biplane x-rays or other imaging techniques producing pairs of conventional planar images of the implanted device and a calibration standard. By initializing the algorithm using a user-specified curved template, highly curved non-linear medical devices can be accurately reconstructed.

Figure 4C:
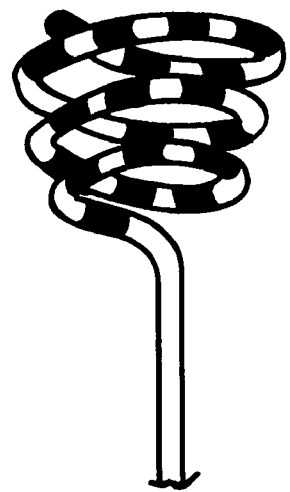
FIGS. 4A-4C are schematic diagrams of a distal end of a non-linear implantable medical device for practicing the present invention.
Figure 4B:
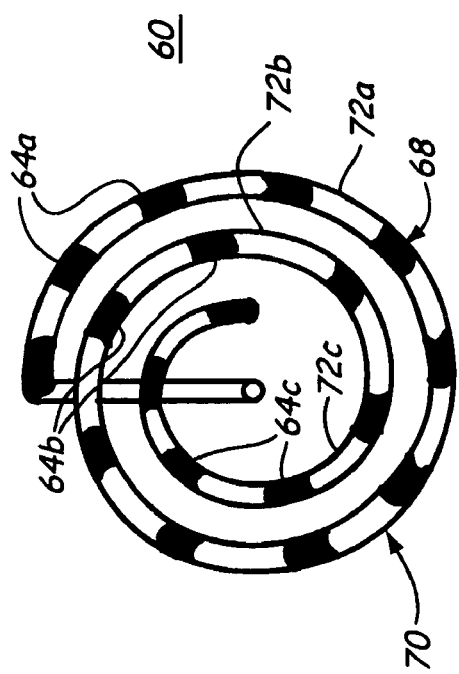
Figure 4A:
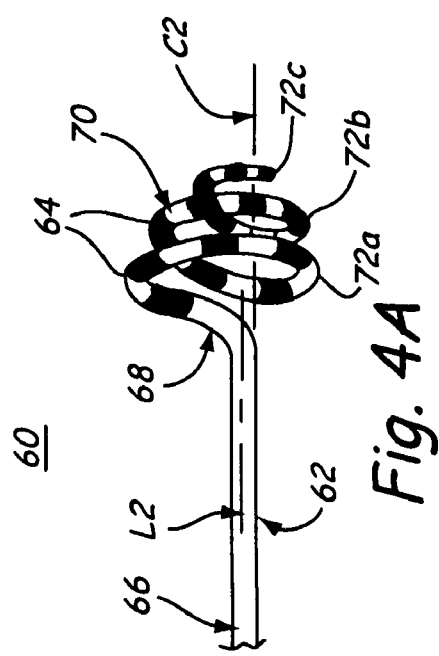

As indicated above, the present invention is directed toward providing a method for reconstructing a dynamic three-dimensional model of an implanted medical device. Such device reconstruction is valuable for designing and validating in vitro testing methods and structural models and assessing in vivo device motion. The methods included herein are particularly useful for reconstructing an implanted medical device having a highly curved geometry subject to physiological dynamic motion such as cardiac or respiratory motion. The present invention is specifically designed for reconstructing a substantially non-linear medical device, such as an annuloplasty ring or band, subjected to cardiac motion, a catheter having a distal end as illustrated in FIGS. 4A-4C, or a stent, for example.

Figure 1:
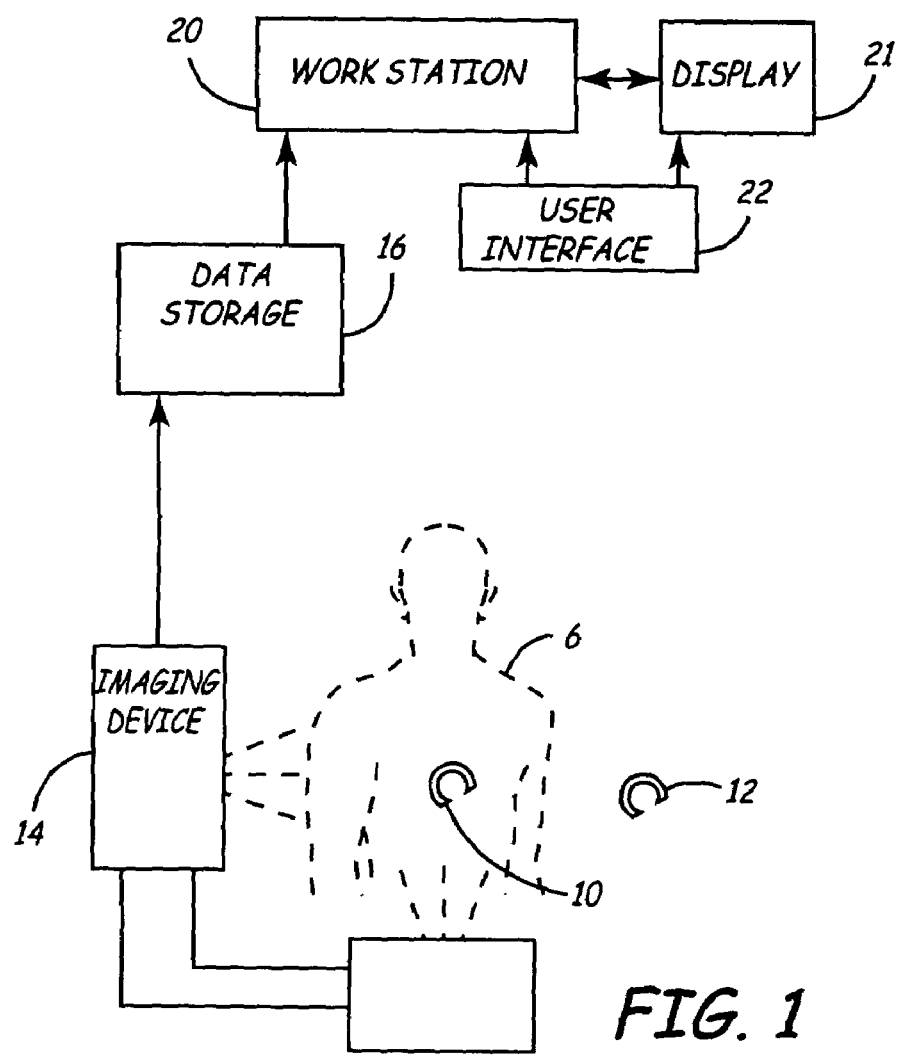
FIG. 1 is a schematic diagram of a system for acquiring biplane x-ray images of an implanted medical device and a calibration object and for incorporating image data with user-entered geometry data to generate a four-dimensional reconstruction of the device centerline.

FIG. 1 is a schematic diagram of a system for acquiring biplane x-ray images of an implanted medical device and a calibration object and for incorporating image data with user-entered geometry to generate a four-dimensional reconstruction of the device centerline. The system includes an imaging device 14 for generating biplane images of a medical device 10 implanted in a patient 6 or experimental subject. In a preferred embodiment, imaging device 14 is a biplane radiographic imaging device. Biplane views of the imaging field are simultaneously recorded, and image data are stored by data storage unit 16 or acquired directly to a personal computer or work station 20. Images stored in a desired format by data storage unit 16, e.g., video, film or digital format, are later transferred to work station 20 for subsequent computer analysis.

Reconstruction of the implanted device is derived from a biplanar device image, and device motion can be measured by reconstructing the device at each point in time during an imaging sequence. The rate of image acquisition and the duration of the imaging sequence are determined according to the application. For analysis of non-linear medical device motion, an imaging sequence over one cardiac cycle is typically desired.

Software for processing image data is implemented in a personal computer or work station 20, with image data transferred from the data storage unit 16 to work station 20. Work station 20 includes a display 21 for displaying acquired biplane images and the evolution of the implanted device reconstruction. Work station 20 is also provided with a user interface 22 for receiving user-entered data regarding device geometry, as will be further described below.

Figure 2:
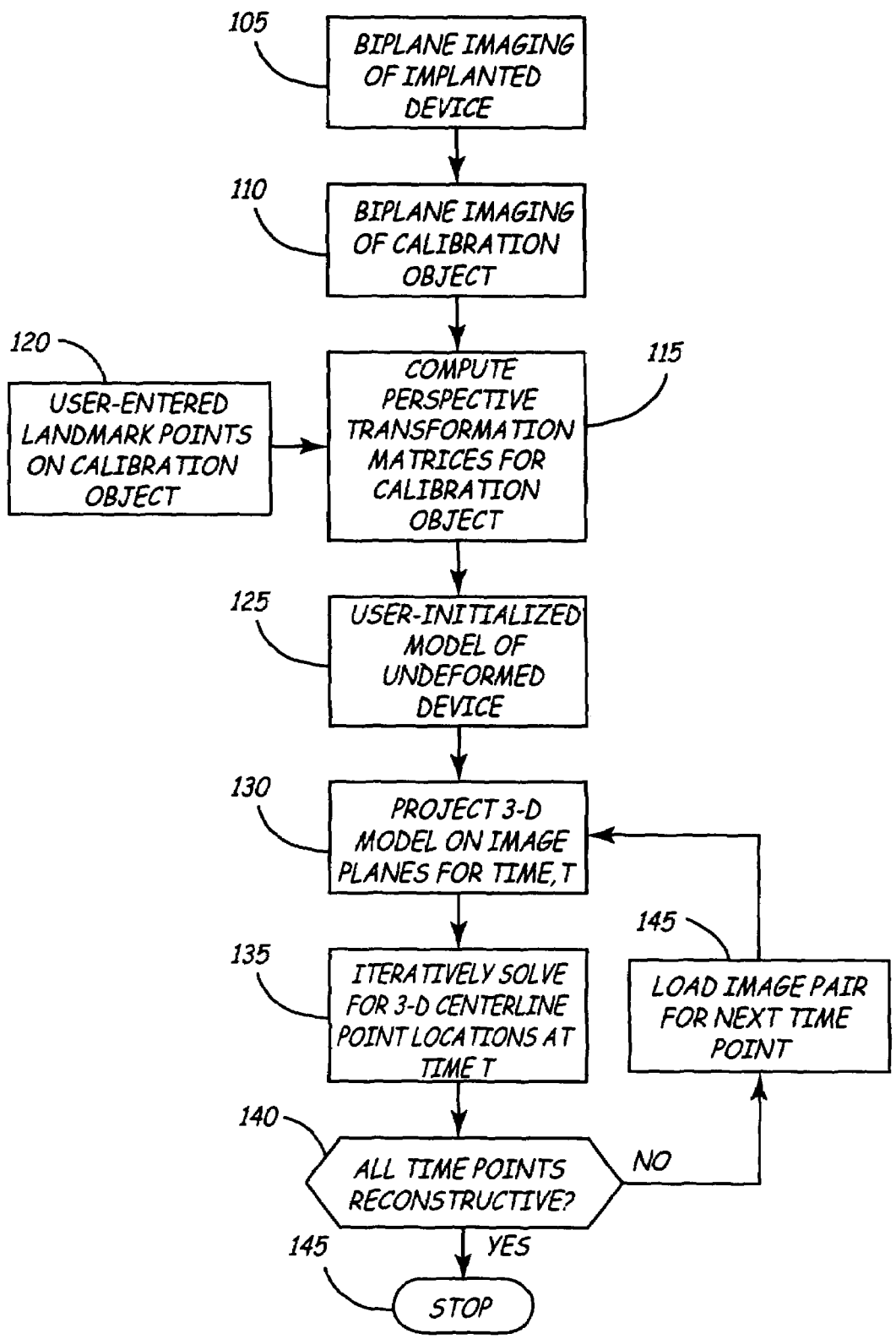
FIG. 2 is a flow chart summarizing the steps included in an algorithm, which may be implemented using the system of FIG. 1, for generating a four-dimensional reconstruction of an implanted non-linear medical device centerline.

FIG. 2 is a flow chart summarizing the steps included in an algorithm which may be implemented using the system of FIG. 1 for generating a four-dimensional reconstruction of an implanted non-linear medical device centerline. At step 105, biplane radiographic imaging of the implanted device is performed, with image data stored and/or transferred as described above. An imaging sequence may correspond to one or more cardiac cycles or cardiac cycle segments or respiratory cycles or cycle segments or other time duration that captures the device motion and deformation of interest. Immediately after biplane images of the implanted non-linear medical device are acquired, a calibration object is placed in the imaging volume without altering the imaging geometry to record biplane images of the calibration object, as indicated at step 110.

At step 115, calibration of the biplane imaging volume is performed by computing perspective transformation matrices using images of the calibration object. The transformation matrices relate the three-dimensional coordinates of the volume occupied by the calibration object to each imaging plane's local two-dimensional image coordinates. See Mackay S A, et al., Comput. Biomed. Res. 1982:15: 455-473 for technical details regarding this transformation, incorporated herein by reference in its entirety. The transformation matrices are calculated using estimates based on user-specified image coordinates of landmark points on the calibration object from each biplane image and known three-dimensional coordinates of the landmark points on the object. User-specified points are entered at step 120 as input to the calibration process. The resulting transformation relationships can be expressed by:

$$x_{i[G]}^1 = k^1 u_j^1, \text{ and } x_i[G]^2 = k^2 u_j^2$$

wherein $x_i$ represents the global coordinates with i equaling 1, 2 or 3 corresponding to the three dimensions of the global volume; $[G]^1$ and $[G]^2$ represent 4×3 matrices corresponding to the first and second planar views, respectively; $k^1$ and $k^2$ are scaling factors relating to the magnification of a particular view and $u_j^1$ and $u_j^2$ represent the local coordinates of the first and second planar views, respectively, with j equaling 1 or 2 corresponding to the two dimensions of the respective planar view.

At step 125, a user-specified, curved template of the undeformed implanted device is provided as input to initialize the active contour evolution process. The user-intialized reconstruction permits an iterative process to begin with a curved non-linear medical device template enabling accurate device reconstruction. The curved non-linear device could include implantable medical devices such as a catheter, a stent, or heart valve device, for example. The user selects, via user interface 22 (FIG. 1), two or more fiducial points on or near the images of the device to orient the three-dimensional curved device template. Points may correspond to identifiable landmarks on the medical device such as device endpoints, joints of dissimilar materials, recognizable device component locations, or on a starting point not located directly on the device, such as a point corresponding to a center of radius 13 (FIG. 1) of the non-linear device.

Figure 3:
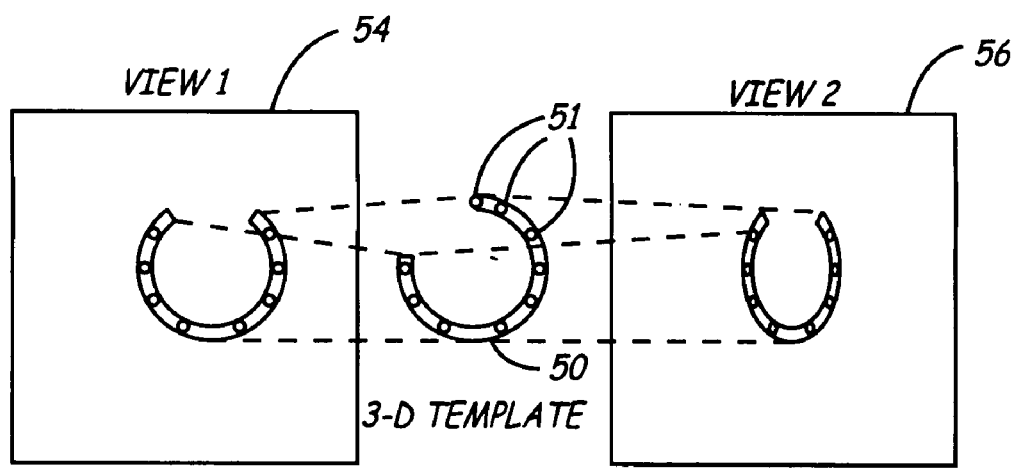
FIG. 3 is a schematic illustration of a user-initialized curved model of an annuloplasty band projected on two imaging planes.

At step 130, the three-dimensional curved template is projected onto the first of the time-paired image planes. FIG. 3 is a schematic illustration of a user-initialized curved model of an annuloplasty band projected on two imaging planes. In order to solve for a three-dimensional model point without requiring user intervention, it is necessary to project spatial positions of a three-dimensional model onto local image coordinates and iteratively solve for the three-dimensional coordinates rather than deriving the three-dimensional global points from two sets of local projection coordinates. As shown in FIG. 3, active contour model points 51 along the centerline of the user-initialized template 50 are projected onto each biplane image 54 and 56. Projection of three-dimensional centerline points onto each two-dimensional view is achieved using the corresponding transformation perspective matrices computed previously at step 115.

At step 135, an iterative algorithm is performed to solve for the three-dimensional centerline point coordinates for the given time point corresponding to the first pair of planar images. The solution algorithm preferably employs an active contour method. During solution iterations, the user can interactively prod projected points in each view with a mouse or other pointing device.

After finding the centerline coordinates for the current image pair, the next pair of images is loaded at step 145 for determining the centerline location of the implanted non-linear medical device at the next recorded time point. Steps 130 and 135 are repeated until the coordinates for points along the implanted non-linear medical device centerline are calculated for all instants in time recorded during a selected imaging sequence as determined at decision step 140, after which the algorithm is terminated at step 145. An example of an algorithm for performing all of the steps described in FIG. 2, other than the step of generating the user-specified curved non-linear medical device template (Step 125) can be found in chapter 2 of Baxter W W, et al., Medical Image Analysis 2001, incorporated herein by reference in its entirety.

Once the displacements of the device centerline over a given time interval are known, the centerline coordinate data may be provided as input for a number of analyses. Displacement and shape change measurement data can be used for designing and validating in vitro testing and structural modeling methods or for clinical evaluation of in vivo device motion. Displacement and deformation data is generated based on clinically realistic device imaging and known device geometry thereby providing a powerful framework for device design work and testing.

Thus, a system and method has been described which allow accurate dynamic three-dimensional reconstruction of an implanted non-linear medical device centerline. Results are valuable to engineers and scientists in designing new non-linear medical devices and developing physically realistic in vitro tests to attempt to ultimately improve overall device performance. For example, such results can be used in test developments, structural analysis, boundary conditions for generating models, or as an input to implantable stimulation devices. Specific embodiments have been described herein to illustrate features of the invention with respect to a particular medical device. While the present invention has been described according to specific embodiments in the above disclosure, these embodiments should be considered exemplary, rather than limiting, with regard to the following claims.

The invention claimed is:

1. A system for reconstructing a dynamic, three-dimensional contour model of a non-linear shaped implanted medical device, comprising:
   an imaging device generating biplane imaging data of an implanted medical device;
   a data storage unit storing the generated biplane imaging data;
   a computer work station processing the stored image data, the work station including a display for displaying acquired biplane images and for displaying the implanted device contour model;
   a user interface coupled to the work station receiving user-entered data regarding implanted medical device geometry including a user-specified, curved non-linear template corresponding to the non-linear implanted medical device prior to implantation; and
   means resident on the work station for directing the execution of an iterative process of implanted medical device contour model that begins with the user-specified, curved non-linear template,
   wherein the means resident on the work station for directing the execution of an iterative process of implanted medical device contour model includes means for orienting the template along an image of the implanted medical device based upon user selection of a plurality of points along the image and generates three-dimensional centerline point coordinates for a pair of biplane images of the implanted medical device.

2. The system of claim 1, wherein the selected plurality of points correspond to identifiable landmarks of the implanted medical device.

3. The system of claim 1, wherein at least one point of the selected plurality of points is offset from the implanted medical device.

4. The system of claim 3, wherein the at least one point corresponds to a center of radius of the implanted medical device.

5. The system of claim 1, wherein the implanted medical device is one of a catheter, a stent and a heart valve device.

6. The system of claim 1, wherein the biplane imaging data comprises a plurality of time-paired image planes obtained during an imaging sequence.

7. The system of claim 6, wherein the imaging sequence comprises at least one cardiac cycle.

8. The system of claim 6, wherein the execution of an iterative process of implanted medical device contour model is made at each point in time during an imaging sequence.

9. The system of claim 1, wherein active contour model points along the centerline of the template are projected onto each of two biplane images of the implanted medical device.

10. The system of claim 1, wherein the means resident on the work station for directing the execution of an iterative process of implanted medical device contour model generates three-dimensional centerline point coordinates for a second pair of biplane images of the implanted medical device after generating three-dimensional centerline point coordinates for the first pair of biplane images of the implanted medical device.

11. The system of claim 1, wherein
   the biplane imaging data comprises a plurality of time-paired image planes obtained during an imaging sequence, each of the plurality of time-paired image planes being acquired at points in time during the sequence; and
   the execution of an iterative process of implanted medical device contour model is made for each of the plurality of time-paired image planes acquired during the imaging sequence.

12. The system of claim 11, wherein the means resident on the work station for directing the execution of an iterative process of implanted medical device contour model generates three-dimensional centerline point coordinates for each of the plurality of time-paired image planes acquired during the imaging sequence of the implanted medical device.

* * * * *